US00PP24441P3

(12) United States Plant Patent
Rockwood

(10) Patent No.: US PP24,441 P3
(45) Date of Patent: May 13, 2014

(54) ***EUCALYPTUS* TREE NAMED 'G5'**

(50) Latin Name: *Eucalyptus grandis*
Varietal Denomination: G5

(75) Inventor: Donald L. Rockwood, Gainesville, FL (US)

(73) Assignee: Florida Foundation Seed Producers, Inc., Marianna, FL (US)

( * ) Notice: Subject to any disclaimer, the term of this patent is extended or adjusted under 35 U.S.C. 154(b) by 54 days.

(21) Appl. No.: 13/385,867

(22) Filed: Mar. 9, 2012

(65) Prior Publication Data

US 2013/0239268 P1 Sep. 12, 2013

(51) Int. Cl.
*A01H 5/00* (2006.01)

(52) U.S. Cl.
USPC ..... Plt./216

(58) Field of Classification Search
USPC ..... Plt./216
See application file for complete search history.

(56) References Cited

U.S. PATENT DOCUMENTS

PP21,570 P2 12/2010 Rockwood

*Primary Examiner* — Kent L Bell
(74) *Attorney, Agent, or Firm* — Dentons US LLP

(57) ABSTRACT

A new *Eucalyptus grandis* tree particularly distinguished by having a fast growth rate, average frost tolerance, and good coppicing properties, is disclosed.

7 Drawing Sheets

ACKNOWLEDGEMENT OF FEDERAL RESEARCH SUPPORT

This invention was supported in part by funds from the U.S. Government pursuant to Grant No. FLA-FOR-04168 from USDA CSREES. The U.S. Government therefore has certain rights in the invention.

Latin name of the genus and species of the plant claimed: *Eucalyptus grandis*.

Variety denomination: 'G5'.

BACKGROUND OF THE INVENTION

The present invention comprises a new and distinct variety of *Eucalyptus*, botanically known as *Eucalyptus grandis*, and hereinafter referred to by the variety name 'G5'. It is characterized by having a fast growth rate, average frost tolerance, and good coppicing properties when grown under normal forestry practices in southern Florida.

SUMMARY OF THE INVENTION

'G5' originated from over 1,600 seedlings of *Eucalyptus grandis*. 'G5' is the result of open-pollination in a fourth-generation seedling seed orchard at Palmdale, Fla. The female (seed) parent of 'G5' is the proprietary *Eucalyptus grandis* seedling selection with the identification number '3242', not patented, characterized by its fast growth and average frost tolerance. The male (pollen) parent of 'G5' is unknown. The maternal parent ('3242') originated from open-pollination. The female (seed) parent of '3242' is the proprietary *Eucalyptus grandis* seedling selection with the identification number '1065', not patented, characterized by its good growth and acceptable frost tolerance. The male (pollen) parent of '3242' is unknown. 'G5' was selected as a single tree from the progeny of the above stated open-pollination during March 2004.

'G5' was first propagated in June of 2008 in Apopka, Fla. through cuttings and in vitro propagation. Asexually propagated trees of 'G5' have remained true to the original selected tree, and all characteristics of the tree have been transmitted and retained through three successive asexual vegetative generations.

Plant Breeder's Rights for this cultivar have not been applied for. 'G5' has not been made publicly available more than one year prior to the filing of this application.

'G5' differs from the female parent '3242' by having faster growth, better frost tolerance, and good coppicing properties.

Commercial varieties: E.nergy™ series *eucalyptus* cultivars 'G1', 'G2', 'G3', and 'G4' may be compared with *eucalyptus* cultivar 'G5' (see Table 1).

TABLE 1

Comparison of *Eucalyptus grandis* Cultivars 'G1', 'G2', 'G3', 'G4', and 'G5'

| | Cultivar | | |
|---|---|---|---|
| | G1[a] | G2[a] | G3[a] |
| Tree: | | | |
| Size: Height (m) | 12.6 | ~15 | ~16 |
| Size: DBH (Diameter in cm at 4.5') | | | |
| Size: Spread (m) | ~4 | ~3 | ~3 |
| Vigor: | Average | Good | Good |
| Density: | Open | Open | Open |
| Form (overall shape of tree): | Good | Good | Good |
| Growth habit (current season): | Evergreen | Evergreen | Evergreen |
| Trunk and Branches: | | | |
| Trunk texture: top | Smooth | Smooth | Smoother |
| Trunk texture: base | Rough | Smooth | Smooth |

TABLE 1-continued

Comparison of *Eucalyptus grandis* Cultivars 'G1', 'G2', 'G3', 'G4', and 'G5'

| | | | |
|---|---|---|---|
| Trunk upper bark color: | Mottled grey-brown | Mottled grey, brown, green | Mottled grey, brown, green |
| Trunk lower bark color: | Mottled grey-brown | Mottled grey, brown, green | Mottled grey, brown, green |
| Branch texture: | Glabrous | Glabrous | Glabrous |
| Branch color: | Green | Green | Green, Reddish |
| Leaves: | | | |
| Size (lamina average): Length (cm) | 10-20 | 10-20 | 10-16 |
| Size (lamina average): Width (cm) | 1.5-3.0 | 1.5-2.5 | 1.5-2.5 |
| Type: | Simple, petiolate, alternate, persistent | Simple, petiolate, alternate, persistent | Simple, petiolate, alternate, persistent |
| Shape: | Narrow lanceolate, slightly sickle shaped | Narrow lanceolate, slightly sickle shaped | Narrow lanceolate, slightly sickle shaped |
| Apex: | Acuminate | Acuminate | Acuminate |
| Base: | Acute, can be slightly unequilateral | Acute, can be slightly unequilateral | Acute, can be slightly unequilateral |
| Margin: | Smooth | Smooth, Wavy | Smooth, Wavy |
| Surface texture: Upper | Glabrous | Glabrous | Glabrous |
| Surface texture: Lower | Glabrous | Glabrous | Glabrous |
| Color: Upper | Dark green (RHS Green group 126C) | Green (RHS Green group 126C) | Green (RHS Green group 136B) |
| Color: Lower | Light green (RHS Green group 124B) | Green (RHS Green group 127B) | Green (RHS Green group 136C) |
| Petiole: Shape | Slightly flattened, groove at top | Slightly flattened, groove at top | Slightly flattened, groove at top |
| Petiole: Length (cm) | 1.5-2.5 | 1.5-2.0 | 1.5-2.5 |
| Petiole: Width (mm) | 1-2 | 1-2 | 1-2 |
| Petiole: Upper Color | Pale green (RHS Yellow-Green group 144D) | Pale green (RHS Yellow-Green group 144D) | Pale green (RHS Yellow-Green group 144D) |
| Petiole: Lower Color | Pale green (RHS Yellow-Green group 144D) | Pale green (RHS Yellow-Green group 144D) | Pale green (RHS Yellow-Green group 144D) |
| Petiole: Texture | Smooth | Smooth | Smooth |
| Flowers: | | | |
| Age at First Flowering: (years) | 2+ | 2+ | 2+ |
| Flower Fragrance: | Mild | Mild | Mild |
| Flower Type: | Clustered | Clustered | Clustered |
| Flower Buds/Cluster: | 7 | 7 | 7 |
| Stamen: Number | Many | Many | Many |
| Anther Filament: Length (cm) | <1 | ~1 | ~1 |
| Anther: Color | White | White | White |
| Pistil: Number | 1 | 1 | 1 |
| Pistil: Length (cm) | <1 | <1 | <1 |
| Bloom Season | mid-July-October | late July-mid-September | mid-August-late-October |
| Reproductive Organs: | | | |
| Fruit/seed (if produced): | | | |
| Capsules/Cluster | 3-7 | 3-7 | 3-7 |
| Capsule: Size (mm) | 5-7 × 5-6 | 5-7 × 5-6 | 5-7 × 5-6 |
| Capsule: Shape | Pyriform | Pyriform | Pyriform |

TABLE 1-continued

Comparison of *Eucalyptus grandis* Cultivars 'G1', 'G2', 'G3', 'G4', and 'G5'

| | | | |
|---|---|---|---|
| Capsule: Texture | Smooth Woody | Smooth Woody | Smooth Woody |
| Capsule: Color | Green-brown | Green-brown | Green-brown |
| Capsule Stalk: Length | Short | Short | Short |
| Resistance/tolerance to Diseases/pests: | | | |
| Blue Gum Chalcid | No | Yes | Yes |
| Coppice: | | | |
| Ability | High | High | High |
| Stems/Stool | 3-5 | 1-2 | 3-5 |

| | Cultivar | |
|---|---|---|
| | G4[a] | G5[b] |
| Tree: | | |
| Size: Height (m) | ~16 | ~15.4 |
| Size: DBH (Diameter in cm at 4.5') | | 18.3 |
| Size: Spread (m) | ~3 | ~3 |
| Vigor: | Good | Good |
| Density: | Open | Open |
| Form (overall shape of tree): | Good | Straight Stem, Slightly Drooping Branches |
| Growth habit (current season): | Evergreen | Evergreen |
| Trunk and Branches: | | |
| Trunk texture: top | Smoother | Smooth |
| Trunk texture: base | Smooth | rough |
| Trunk upper bark color: | Mottled grey, pink | Moderate yellow (RHS 161A) to Pale green (RHS 160C) |
| Trunk lower bark color: | Mottled grey, pink | Grayish reddish orange (RHS 176D to RHS 177D) |
| Branch texture: | Glabrous | Glabrous |
| Branch color: | Grey, Reddish | Moderate yellow (RHS 160A) |
| Leaves: | | |
| Size (lamina average): Length (cm) | 10-15 | 13-13.5 |
| Size (lamina average): Width (cm) | 2 | 4.2-5.0 |
| Type: | Simple, petiolate, alternate, persistent | Simple, petiolate, alternate, persistent |
| Shape: | Narrow lanceolate, slightly sickle shaped | Lanceolate, slightly sickle shaped, slightly offcenter midrib |
| Apex: | Acuminate | Acuminate |
| Base: | Typically acute, can be slightly unequilateral, slightly offcenter midrib | Acute, can be slightly unequilateral |
| Margin: | Smooth, Wavy | Smooth |
| Surface texture: Upper | Glabrous | glabrous |
| Surface texture: Lower | Glabrous | glabrous |
| Color: Upper | Green | Strong yellow green (RHS 143A) |
| Color: Lower | Pale Green | Strong yellow green (RHS 143C) |
| Petiole: Shape | Slightly flattened groove at top | Slightly flattened |
| Petiole: Length (cm) | 1-2 | 1.5-2.5 |
| Petiole: Width (mm) | 1-2 | 1-2 |
| Petiole: Upper Color | Light green-Pink | Deep orangish yellow (RHS 163A) |
| Petiole: Lower Color | Light green-Pink | Deep orangish yellow (RHS 163C) |

TABLE 1-continued

Comparison of *Eucalyptus grandis* Cultivars 'G1', 'G2', 'G3', 'G4', and 'G5'

| | | |
|---|---|---|
| Petiole: Texture | Smooth | Smooth |
| Flowers: | | Not Observed |
| Age at First Flowering: (years) | 2+ | 4+ |
| Flower Fragrance: | Mild | Not Observed |
| Flower Type: | Clustered | Not Observed |
| Flower Buds/Cluster: | 7 | Not Observed |
| Stamen: Number | Many | Not Observed |
| Anther Filament: Length (cm) | ~1 | Not Observed |
| Anther: Color | White | Not Observed |
| Pistil: Number | 1 | Not Observed |
| Pistil: Length (cm) | <1 | Not Observed |
| Bloom Season | mid-September-late-October | Not Observed |
| Reproductive Organs: | | Not Observed |
| Fruit/seed (if produced): | | Not Observed |
| Capsules/Cluster | 3-7 | Not Observed |
| Capsule: Size (mm) | 5-7 × 5-8 | Not Observed |
| Capsule: Shape | Pyriform | Not Observed |
| Capsule: Texture | Smooth Woody | Not Observed |
| Capsule: Color | Green-brown | Not Observed |
| Capsule Stalk: Length | Short | Not Observed |
| Resistance/tolerance to Diseases/pests: | | |
| Blue Gum Chalcid | Yes | Yes |
| Coppice: | | |
| Ability | High | Not Observed |
| Stems/Stool | 3-5 | Not Observed |

[a]13-year-old trees near Ft Meade, FL, and 2-year-old trees near Winter Garden, FL.
[b]4.2-year-old trees near Winter Garden, FL.

BRIEF DESCRIPTION OF THE DRAWINGS

This new *eucalyptus* tree is illustrated by the accompanying photographs which show the tree's form and foliage. The colors shown are as true as can be reasonably obtained by conventional photographic procedures. The photographs are of trees approximately 2 to 3.5-years old.

DETAILED BOTANICAL DESCRIPTION

Figure 1:
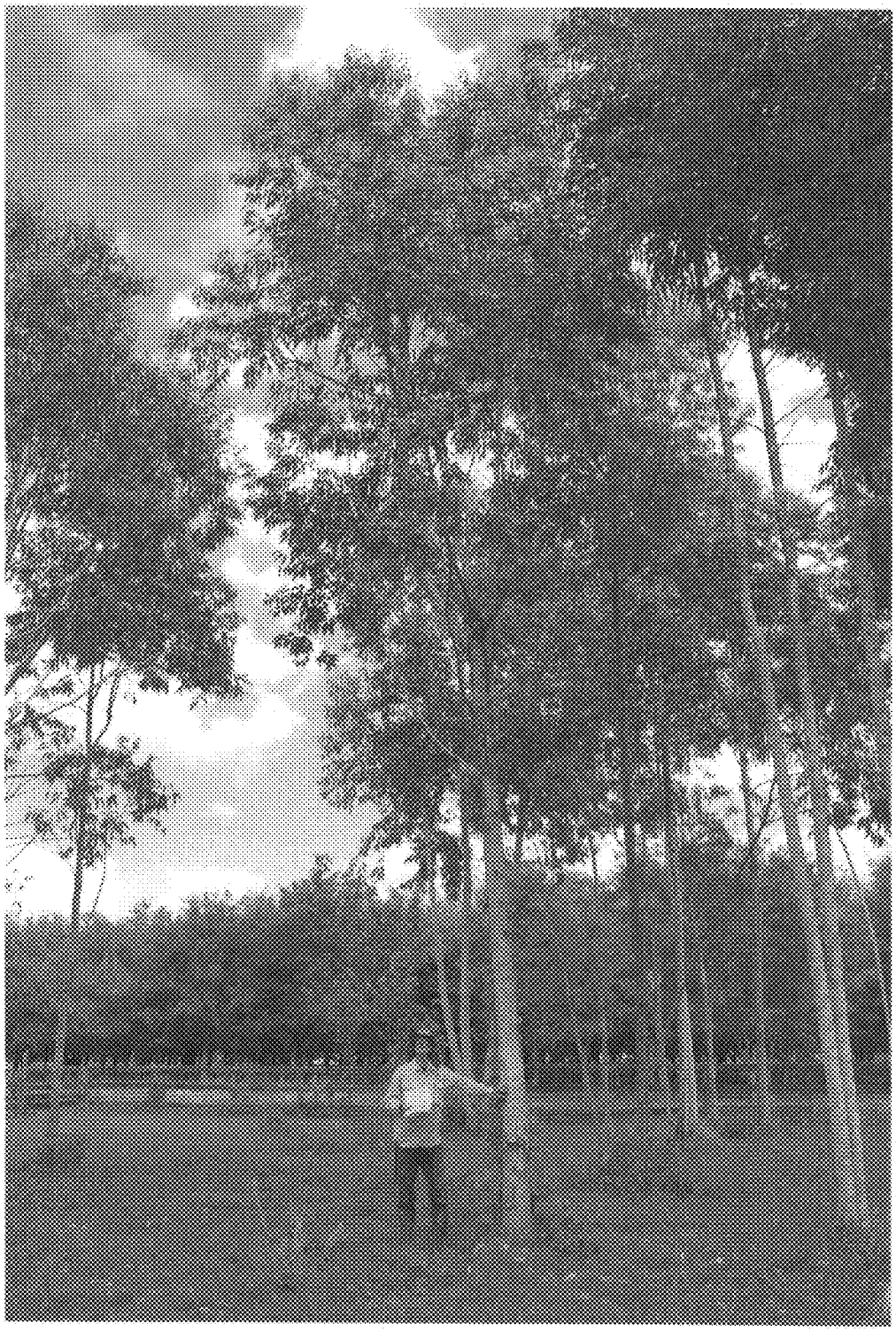
FIG. 1. Shows overall plant habit including foliage of a 3.5-year-old tree.
Figure 2:
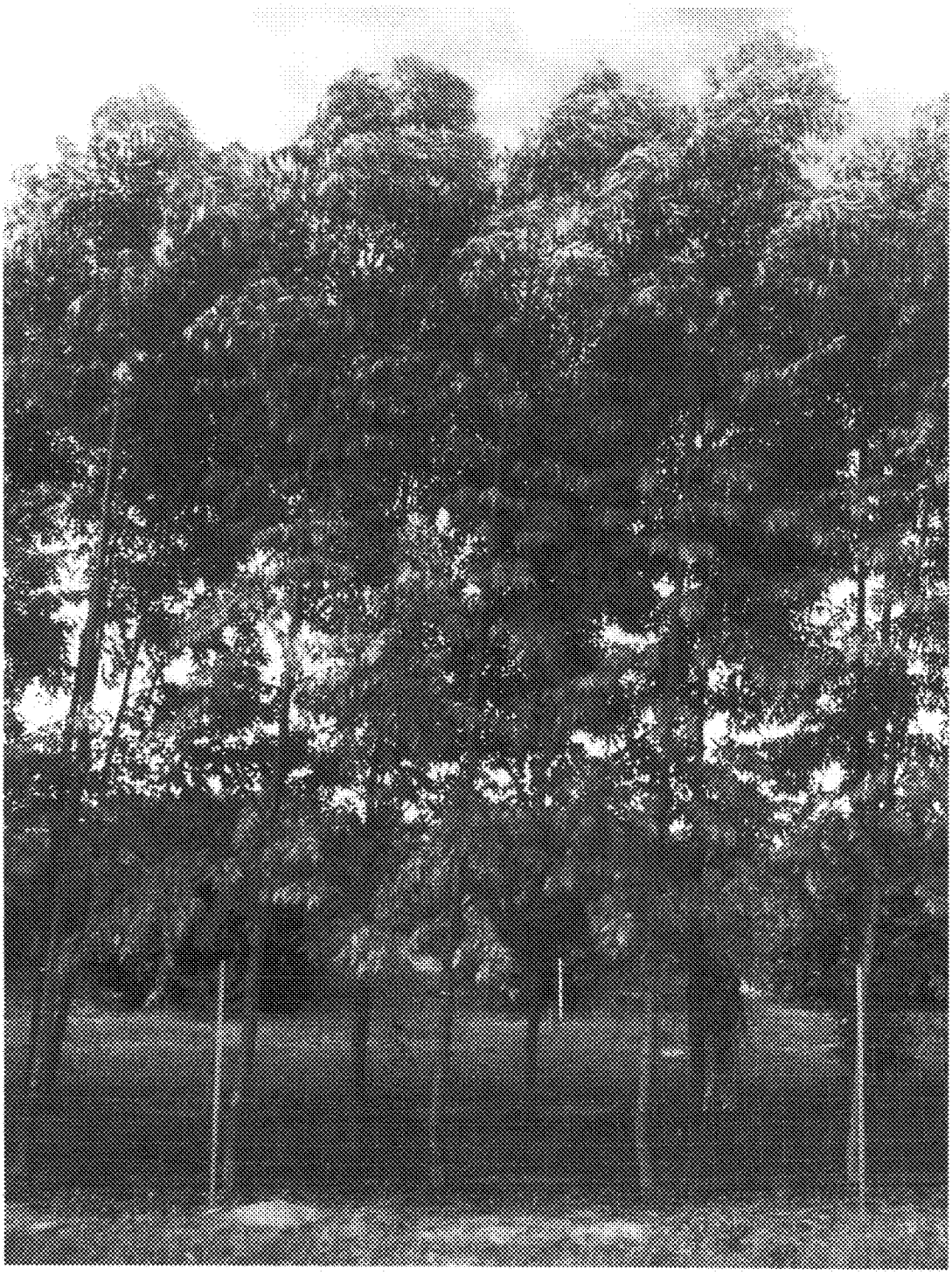
FIG. 2. Shows overall plant habit including foliage of 2-year-old trees.
Figure 3:
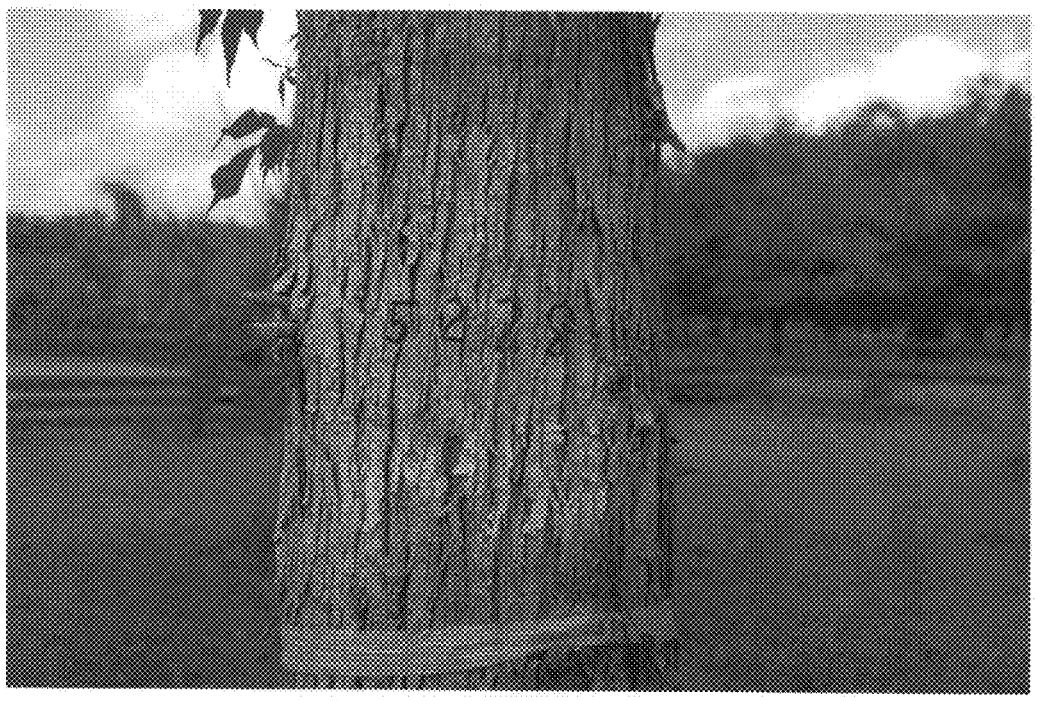
FIG. 3. Shows a close-up of the bark of a 3.5-year-old tree.
Figure 4:
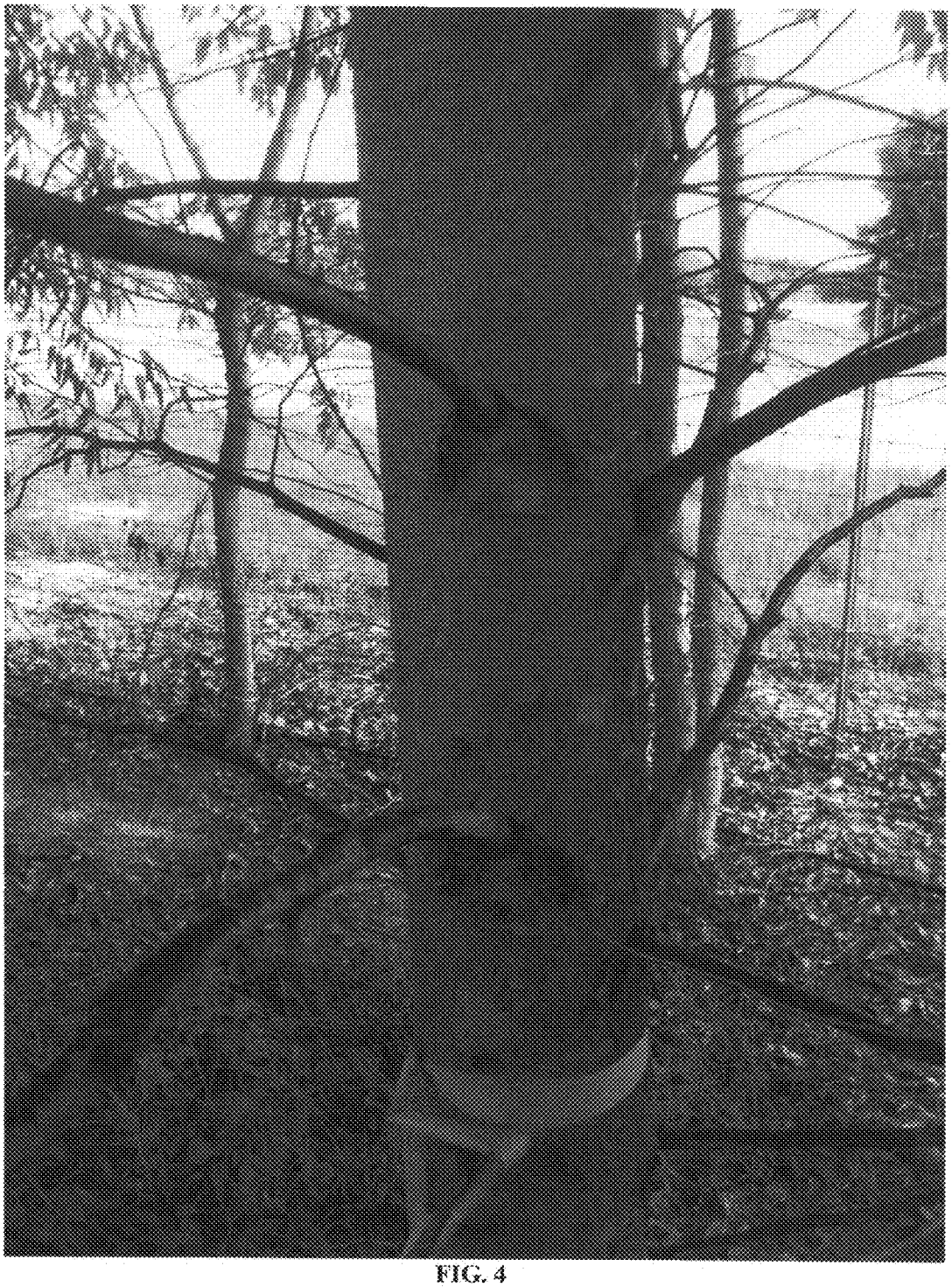
FIG. 4. Shows a close-up of the bark of a 2-year-old tree.
Figure 5:
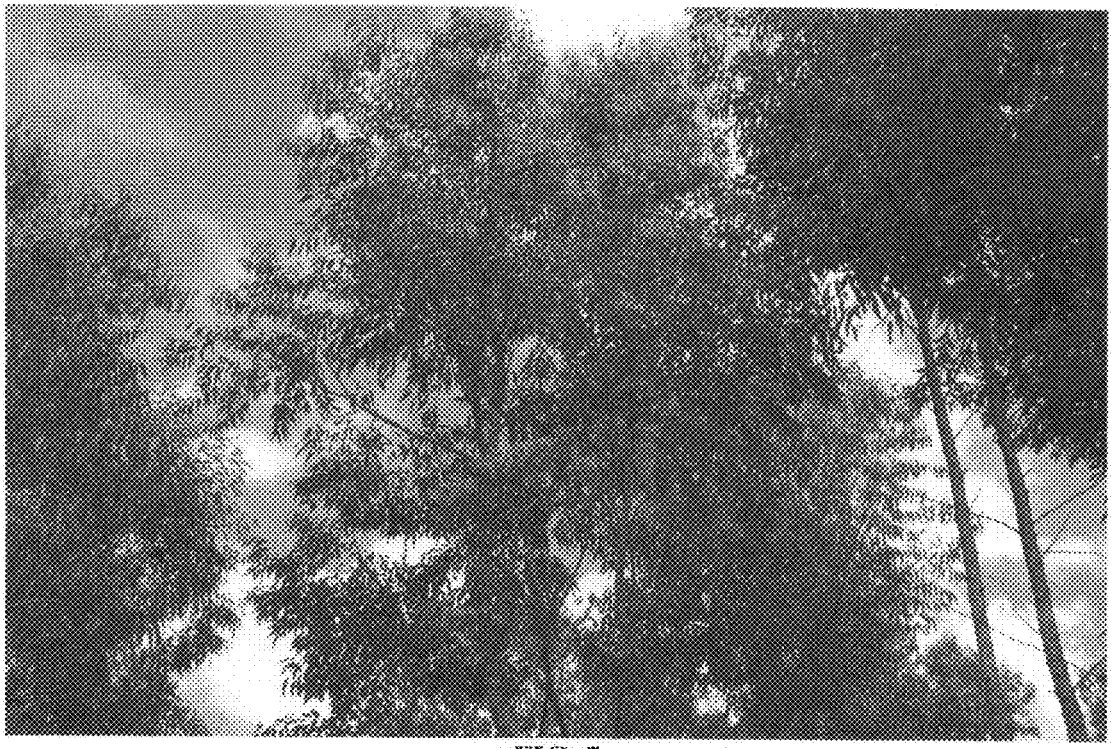
FIG. 5. Shows upper branches of a 3.5-year-old tree.
Figure 6:
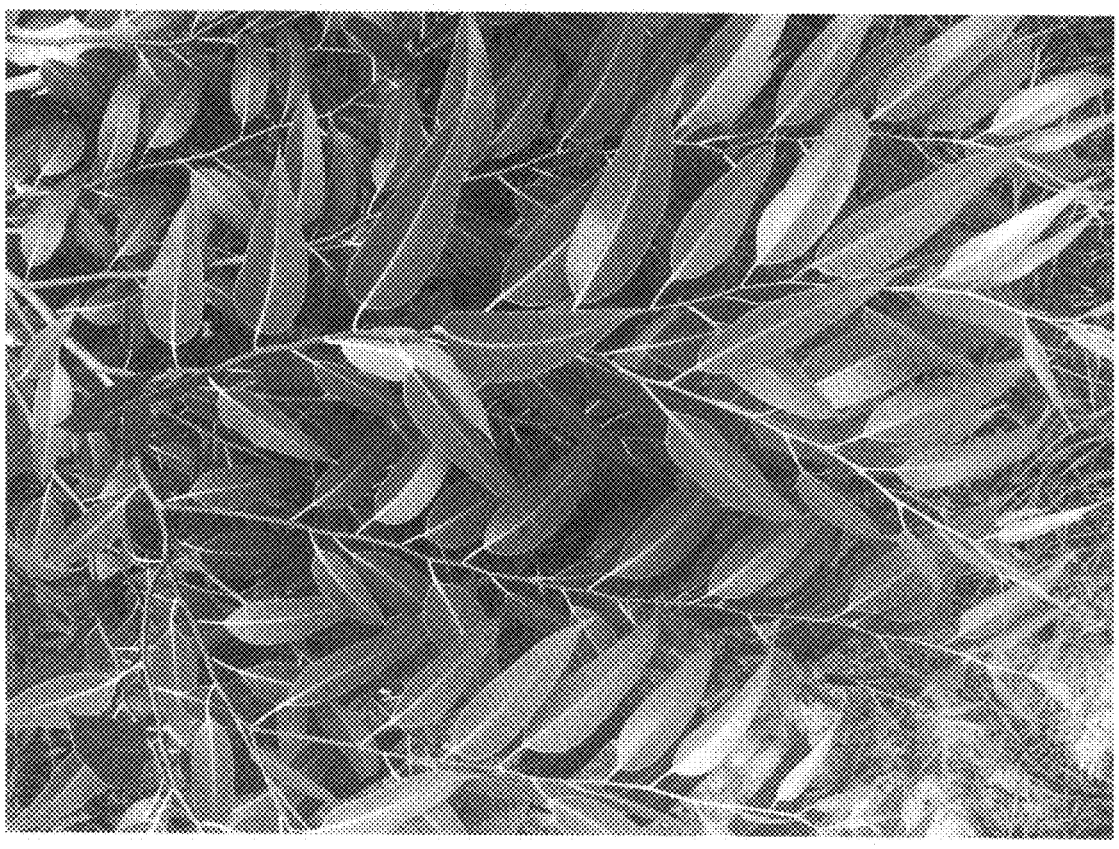
FIG. 6. Shows mature leaves of a 2-year-old tree.
Figure 7:
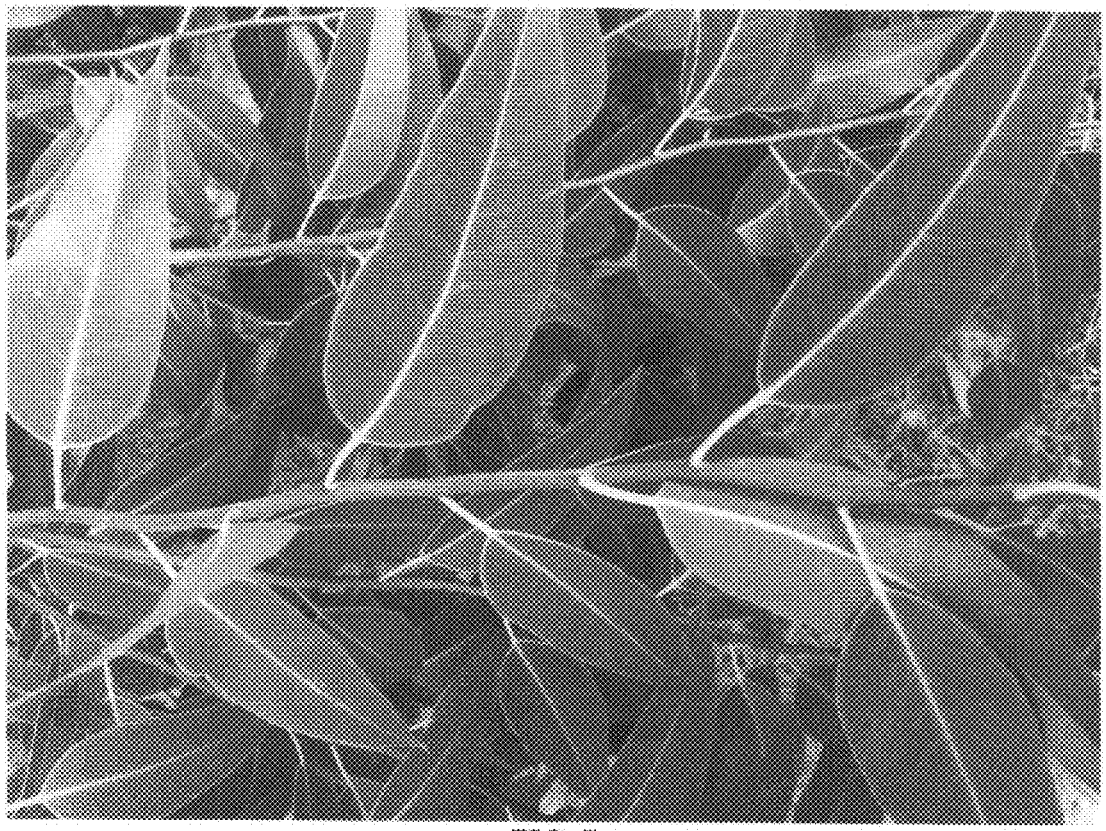
FIG. 7. Shows a close-up of mature leaves of a 2-year-old tree.

The following detailed description sets forth the distinctive characteristics of 'G5'. The present botanical description is that of 2-year-old trees growing near Winter Garden, Fla. The colors (except those in common terms) are described from R.H.S. Colour Chart published by The Royal Horticultural Society in London (second edition), in association with the Flower Council of Holland.

Phenotypic Description of *Eucalyptus grandis* var. 'G5'

Classification:

*Botanical.*—*Eucalyptus grandis* var. 'G5'.

*Common name.*—*Eucalyptus.*

Parentage:

*Female parent.*—'3242', not patented.

*Male parent.*—Unknown.

Tree:

*Size.*—Height — ~10 m, Spread — ~3 m.

*Vigor.*—Average.

*Density.*—Open.

*Form* (*overall shape of tree*).—Straight stem with slightly drooping branches.

*Growth habit* (*current season*).—Evergreen.

Trunk and branches:

*Trunk diameter.*—18.3 cm at 4.5 feet above the ground.

*Trunk texture.*—Smooth at top, rough at base.

*Trunk upper bark color.*—Moderate yellow (RHS 161A) to Pale green (RHS 160C).

*Trunk lower bark color.*—Grayish reddish orange (RHS 176D to RHS 177D).

*Branch texture.*—Glabrous.

*Branch color.*—Moderate yellow (RHS 160A).

Leaves:

*Size* (*lamina average*).—Length — 10-14 cm, Width 2.0-3.5 cm.

*Type.*—Simple, petiolate, alternate, persistent.

*Shape.*—Lanceolate, slightly sickle shaped, slightly off-center midrib.

*Apex.*—Acuminate.

*Base.*—Acute, can be slightly unequilateral.

*Margin.*—Smooth.

*Surface texture.*—Upper — glabrous, Lower — glabrous.

*Color.*—Upper — RHS 132B (Strong green), Lower — RHS 124B (Light green).

*Petiole.*—Shape: Slightly flattened. Length: 1.5-2.5 cm. Width: 1-2 mm. Color: RHS 11D (Pale yellow). Texture: Smooth.

Flowers: No flowering has been observed.

Reproductive organs: No organs observed.

Fruit/seed (if produced): No fruit/seed observed.

Resistance/tolerance to diseases/pests: No unusual susceptibilities noted.

What is claimed is:

1. A new and distinct variety of *Eucalyptus grandis* tree as shown and described herein.

* * * * *